US006623531B2

(12) United States Patent
Ohashi et al.

(10) Patent No.: US 6,623,531 B2
(45) Date of Patent: Sep. 23, 2003

(54) HAIR DYE COMPOSITION

(75) Inventors: Yukihiro Ohashi, Sumida-ku (JP);
Hajime Miyabe, Sumida-ku (JP);
Kenichi Matsunaga, Sumida-ku (JP)

(73) Assignee: Kao Corporation, Tokyo (JP)

( * ) Notice: Subject to any disclaimer, the term of this patent is extended or adjusted under 35 U.S.C. 154(b) by 163 days.

(21) Appl. No.: 09/891,201

(22) Filed: Jun. 26, 2001

(65) Prior Publication Data

US 2002/0038483 A1 Apr. 4, 2002

(30) Foreign Application Priority Data

Jun. 27, 2000 (JP) ........................................ 2000-193186

(51) Int. Cl.[7] ................................................ A61K 7/13
(52) U.S. Cl. ...................... 8/405; 8/406; 8/451; 8/455; 8/568; 8/573; 8/655; 8/657; 8/659
(58) Field of Search ............................ 8/405, 406, 449, 8/451, 455, 568, 573, 655, 657, 659

(56) References Cited

U.S. PATENT DOCUMENTS

| | | | | |
|---|---|---|---|---|
| 5,733,343 A | | 3/1998 | Mockli | 8/426 |
| 5,879,412 A | * | 3/1999 | Rondeau et al. | 8/411 |
| 5,888,252 A | * | 3/1999 | Mockli | 8/426 |
| 5,980,587 A | | 11/1999 | Samain | 8/426 |

FOREIGN PATENT DOCUMENTS

| | | |
|---|---|---|
| JP | 6-271435 | 9/1994 |
| JP | 8-501322 | 2/1996 |
| JP | 8-507545 | 8/1996 |
| JP | 10-502946 | 3/1998 |
| JP | 10-194942 | 7/1998 |

OTHER PUBLICATIONS

Y. Hishiki, vol. 32, No. 12, pp. 971–988, "Recent Progress in Cyanine Dyes Syntheses," 1974 (with English translation).

* cited by examiner

Primary Examiner—Yogendra N. Gupta
Assistant Examiner—Eisa Elhilo
(74) Attorney, Agent, or Firm—Oblon, Spivak, McClelland, Maier & Neustadt, P.C.

(57) ABSTRACT

The invention relates to a hair dye composition having markedly high dyeing power, less color fade over time, and undergoes a small change in the color tone of the dye even after storage.

14 Claims, No Drawings

HAIR DYE COMPOSITION

TECHNICAL FIELD

The present invention relates to a hair dye composition having markedly high dyeing power, can strongly impart the hair with an extremely vivid color ranging from yellow, red, blue to green, has less color fade over time and undergoes a small change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that when a cation group is contained in an azo-based (—N=N—) conjugated system, they are unstable to an alkali agent or a reducing agent essentially contained in a permanent hair dye.

DISCLOSURE OF THE INVENTION

An object of the present invention is to provide a hair dye composition which has high hair dyeing power, less color fade over time, and excellent storage stability to permit only a small change in color tone of the dye after storage.

The present inventors have found that when the below-described compounds known as photosensitizing dye or sensitizing dye [Journal of Synthetic Organic Chemistry, Japan, 32(12), 971–988 (1974), etc.] are used as a hair dye, the resulting dye composition can strongly impart the hair with a vivid color ranging from yellow, red, blue to green without decomposing the dye upon hair drying, exhibits excellent light resistance, washing resistance, perspiration resistance, friction resistance and heat resistance, and undergoes a small change in the color tone of the dye after storage as compared with that rightly after preparation because the dye exists in the composition stably.

In one aspect of the present invention, there is thus provided a hair dye composition comprising, as a direct dye, a compound represented by the following formula (I), (II), (III) or (IV):

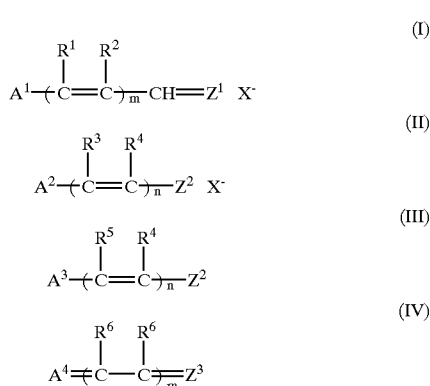

wherein, m stands for 0, 1 or 2, n stands for 1 or 2, m units of $R^1$ and n units of $R^4$ each independently represents a hydrogen atom, a $C_{1-4}$ alkyl group or a halogen atom, m units of $R^2$ each independently represents a hydrogen atom, a $C_{1-4}$ alkyl group or an aryl group, with the proviso that at m=2, two $R^2$s, taken together with the adjacent =C—CH=C—, may form a carbocyclic structure or an oxygen-containing heterocyclic structure, n units of $R^3$ each independently represents a hydrogen atom or a $C_{1-4}$ alkyl group, n units of $R^5$ each independently represents a hydrogen atom or a $C_{1-4}$ alkyl group, or is bonded, via a group —CO—O—, to a ring $B^5$ to form a lactone ring, $R^6$ represents a hydrogen atom or a $C_{1-4}$ alkyl group, $A^1$ represents the below-described formula (1), (2) or (3), $A^2$ represents the below-described formula (4), $A^3$ represents the below-described formula (5), (6), (7), (8) or (9), $A^4$ and $Z^1$ each independently represents the below-described formula (10), (11), (12), (13), (14), (15) or (16), $Z^2$ represents the below-described formula (17), $Z^3$ represents the below-described formula (18), (19), (20) or (21):

$A^1$:

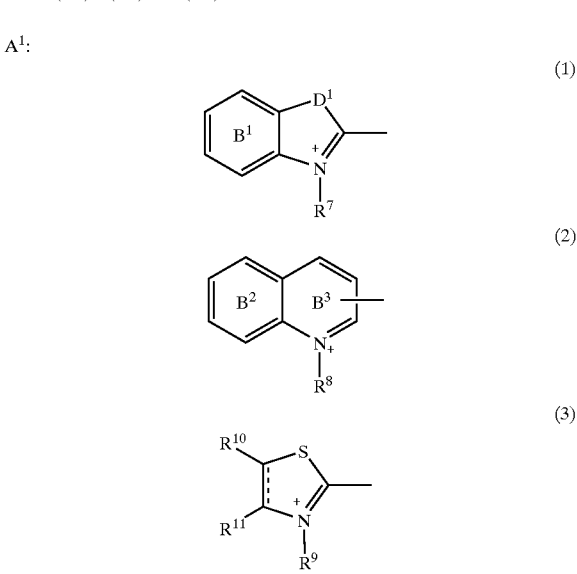

A²:

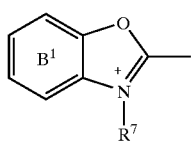 (4)

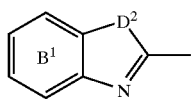 (5)

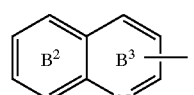 (6)

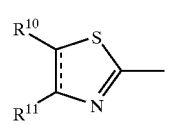 (7)

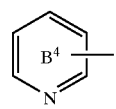 (8)

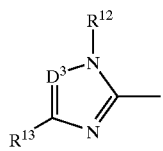 (9)

A⁴, Z¹:

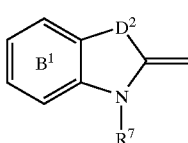 (10)

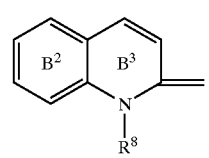 (11)

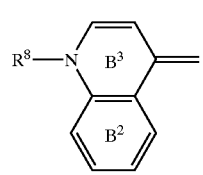 (12)

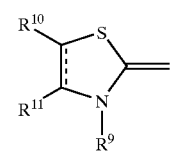 (13)

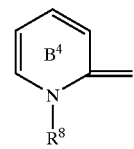 (14)

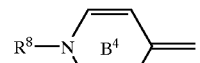 (15)

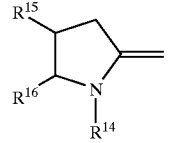 (16)

Z²:

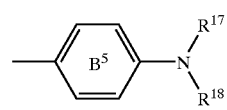 (17)

Z³:

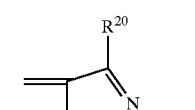 (18)

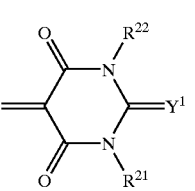 (19)

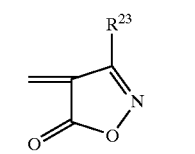 (20)

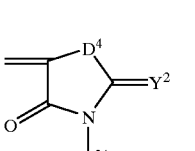 (21)

(in which, a broken line means presence or absence of π bonding, $D^1$ represents an oxygen atom, a sulfur atom or a group $NR^{25}$, $D^2$ represents an oxygen atom, a sulfur atom, a group $NR^{26}$ or a group $CR^{27}R^{28}$, $D^3$ represents a nitrogen atom or a group $CR^{29}$, $D^4$ represents an oxygen atom, a sulfur atom or a group $NR^{30}$, $R^7$, $R^8$, $R^9$, $R^{14}$ and $R^{25}$ each independently represents a $C_{1-6}$ alkyl group which may have a substituent, $R^{10}$, $R^{11}$, $R^{13}$, $R^{15}$, $R^{16}$, $R^{21}$, $R^{22}$, $R^{27}$, $R^{28}$ and $R^{29}$ each independently represents a hydrogen atom or a $C_{1-6}$ alkyl group, $R^{12}$ and $R^{26}$ each independently represents a hydrogen atom or a $C_{1-6}$ alkyl group which may have a substituent, $R^{17}$ and $R^{18}$ each independently represents a hydrogen atom, a $C_{1-6}$ alkyl group which may have a substituent or an aryl group which may have a substituent, or $R^{17}$ and $R^{18}$, taken together with the adjacent nitrogen atom, form a nitrogen-containing heterocycle or one or both of $R^{17}$ and $R^{18}$ is (are) bonded to the ring $B^5$ to form a nitrogen-containing heterocycle, $R^{19}$ and $R^{23}$ each independently represents an aryl group which may have a substituent, $R^{20}$ represents a $C_{1-6}$ alkyl group, $R^{24}$ and $R^{30}$ each independently represents a hydrogen atom, a $C_{1-6}$ alkyl group which may have a substituent, or an aryl group which may have a substituent, $Y^1$ and $Y^2$ each independently represents an oxygen atom or a sulfur atom, rings $B^1$, $B^2$, $B^3$ and $B^4$ each independently has a ring structure which may have, as a substituent, a halogen atom, an aryl group or a $C_{1-4}$ alkyl group or may further be cyclocondensed with a benzene ring, $B^5$ has a ring structure which may have, as a substituent, a halogen atom, an aryl group or a $C_{1-4}$ alkyl group, may be condensed with a benzene ring, or may be bonded to $R^{17}$ or $R^{18}$ to have a ring structure which may be cyclocondensed with a nitrogen-containing heterocycle), and $X^-$ represents an anion, with the proviso that $X^-$ does not exist when $R^7$, $R^8$, $R^9$ and $R^{25}$ each has a sulfonium group as a substituent.

In another aspect of the present invention, there is also provided a method for dyeing the hair with the above-described hair dye composition.

BEST MODE FOR CARRYING OUT THE INVENTION

In the formulas (I) to (IV), m is preferably 0 or 1 and n is preferably 1 from the viewpoint of stability in the hair dye composition.

Examples of the $C_{1-4}$ alkyl group represented by $R^1$ or $R^4$ include methyl, ethyl and butyl groups, those of the halogen atom include chlorine, bromine and fluorine atoms. As each of $R^1$ and $R^4$, a hydrogen atom is most preferred.

Examples of the $C_{1-4}$ alkyl group represented by $R^2$ include methyl, ethyl and butyl groups, those of the aryl group include phenyl group. Examples of the carbocyclic structure which may be formed at m=2 by two $R^2$s when they are taken together with the adjacent =C—CH=C— include cyclohexene ring and cyclopentene ring. As the oxygen-containing heterocyclic structure, 4H-pyrane ring can be mentioned as an example. These rings may be substituted by an alkyl group. As $R^2$, hydrogen atom and $C_{1-4}$ alkyl groups are preferred, of which the hydrogen atom, methyl group and ethyl group are particularly preferred.

Examples of the $C_{1-4}$ alkyl group represented by $R^3$ or $R^6$ include methyl, ethyl and butyl groups. As each of $R^3$ and $R^6$, hydrogen atom is most preferred.

Examples of the $C_{1-4}$ alkyl group represented by $R^5$ include methyl, ethyl and butyl groups, while those of the lactone ring which may be formed by bonding of $R^5$ to the ring $B^5$ via —CO—O— include coumalin ring (including ring $B^5$). As $R^5$, hydrogen atom is most preferred.

As examples of the substituents for the groups (1) to (21) represented by each of $A^1$ to $A^4$ and $Z^1$ to $Z^3$, the below-described ones can be mentioned.

Examples of the $C_{1-6}$ alkyl group represented by $R^7$, $R^8$, $R^9$, $R^{12}$, $R^{14}$, $R^{25}$ or $R^{26}$ include methyl, ethyl, propyl, isopropyl and cyclohexyl groups, which may each be substituted by an aryl (such as phenyl), sulfonium, carboxy or vinyl group. Particularly preferred examples of $R^7$, $R^8$, $R^9$, $R^{14}$ or $R^{25}$ include methyl and ethyl groups, while those of $R^{12}$ and $R^{26}$ include hydrogen atom, methyl group and ethyl group.

Examples of the $C_{1-6}$ alkyl group represented by $R^{10}$, $R^{11}$, $R^{13}$, $R^{15}$, $R^{16}$, $R^{20}$, $R^{21}$, $R^{22}$, $R^{27}$, $R^{28}$ or $R^{29}$ include methyl, ethyl, butyl and hexyl groups. Particularly preferred examples of $R^{10}$, $R^{11}$, $R^{13}$, $R^{15}$, $R^{16}$ and $R^{29}$ include hydrogen atom, those of $R^{20}$, $R^{27}$ or $R^{28}$ include methyl group, and those of $R^{21}$ or $R^{22}$ include hydrogen atom and methyl group.

Examples of the $C_{1-6}$ alkyl group represented by $R^{17}$ or $R^{18}$ include methyl, ethyl, propyl, butyl, hexyl, isopropyl and cyclohexyl groups, which may each be substituted by an aryl group (such as phenyl), cyano group or halogen atom (such as chlorine atom). Examples of the aryl group represented by $R^{17}$ or $R^{18}$ include phenyl and naphthyl groups, which may each be substituted by an amino group. Examples of the ring which may be formed by $R^{17}$ and $R^{18}$ when they are taken together with the adjacent nitrogen atom include pyrrolidine, piperidine, morpholine and piperazine rings. Examples of the nitrogen-containing heterocycle which may be formed by bonding of either one or both of $R^{17}$ and $R^{18}$ to the ring $B^5$ include julolidine ring (including ring $B^5$). Particularly preferred examples of $R^{17}$ or $R^{18}$ include hydrogen atom, methyl group and ethyl group.

Examples of the aryl group represented by $R^{19}$ or $R^{23}$ include phenyl and naphthyl groups, which may each be substituted by a sulfonium group. As each of $R^{19}$ and $R^{23}$, unsubstituted phenyl group is most preferred.

Examples of the $C_{1-6}$ alkyl group represented by $R^{24}$ or $R^{30}$ include methyl, ethyl, propyl, butyl, hexyl, isopropyl and cyclohexyl groups, which may each be substituted by an aryl (such as phenyl), carboxy or vinyl group. Examples of the aryl group represented by $R^{24}$ or $R^{30}$ include phenyl and naphthyl groups, which may each be substituted by a sulfonium group. Particularly preferred as each of $R^{24}$ and $R^{30}$ are hydrogen atom, methyl group and ethyl group.

As each of $Y^1$ and $Y^2$, an oxygen atom is more preferred.

As a substituent for each of the rings $B^1$ to $B^5$, examples of the halogen atom include chlorine, bromine and fluorine atoms, those of the aryl group include phenyl group, and those of the $C_{1-4}$ alkyl group include methyl, ethyl and butyl. As each of the rings $B^1$ to $B^5$, an unsubstituted one is preferred. These rings may each be cyclocondensed with a benzene ring. The ring cyclocondensed with a benzene ring is preferred as well as the above-described uncyclocondensed ring.

Examples of the anion represented by $X^-$ in the formula (I) or (II) include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions and acetic acid ions. When a group ($R^7$, $R^8$, $R^9$ or $R^{25}$) to be bonded to a nitrogen atom has a sulfonium group as a substituent, $X^-$ does not exist because a counterion is formed in the molecule.

In Compounds (I) to (IV), as $A^1$, preferred are the groups (1) (particularly, $D^1$=O, $NR^{25}$) and (2); as $A^3$, preferred are the groups (5) (particularly, $D^2$=O, $NR^{26}$, $CR^{27}R^{28}$), (6) and (8); as $A^4$, preferred are the groups (10) (particularly, $D^2$=O, $NR^{26}$, $CR^{27}R^{28}$), (11), (12), (14) and (15); as $Z^1$, particularly preferred are the group (10) ($D^2$=O) when $A^1$ is the group (1) ($D^1$=O), the group (10) ($D^2$=$NR^{26}$) when $A^1$ is a group (1) ($D^1$=$NR^{25}$), the group (11) when $A^1$ is the group (2) (at 2-position), the group (12) when $A^1$ is a group (2) (at 4-position); and as $Z^3$, preferred are the groups (18), (19) and (21) (particularly, $D^4$=$NR^{30}$). Out of Compounds (I) to (IV), Compounds (I) to (III), particularly Compound (I) is preferred.

Specific examples of the direct dyes (I) to (IV) to be used in the present invention will next be shown.
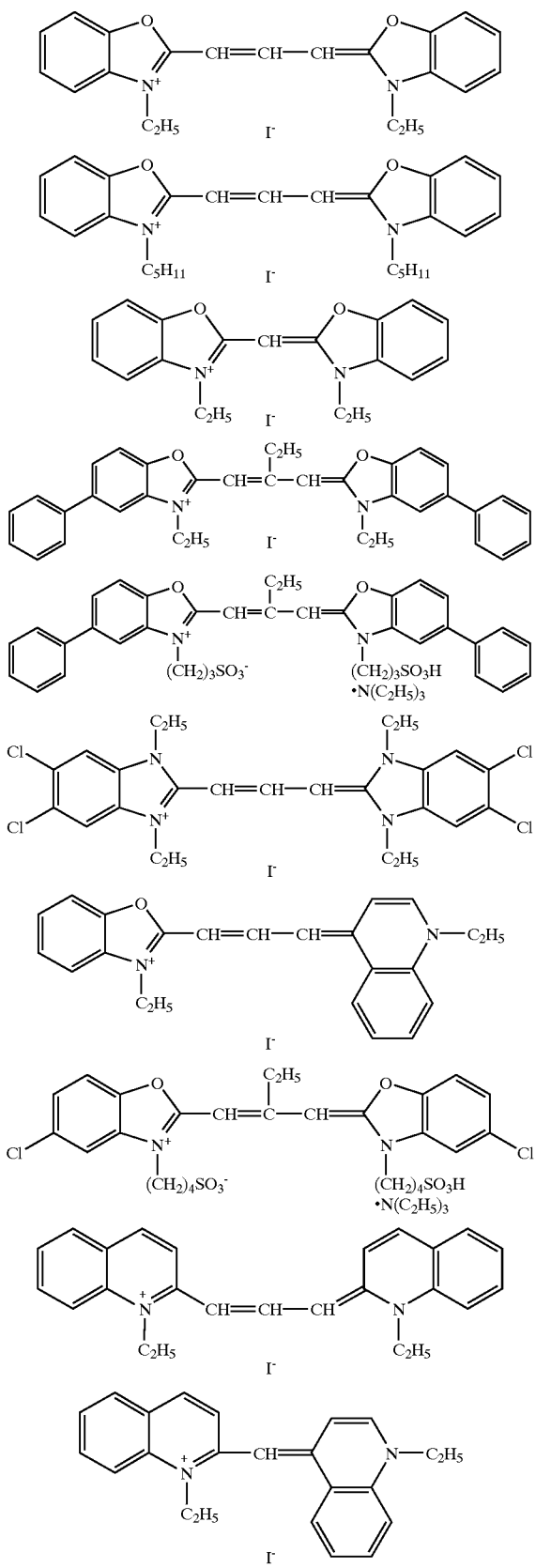
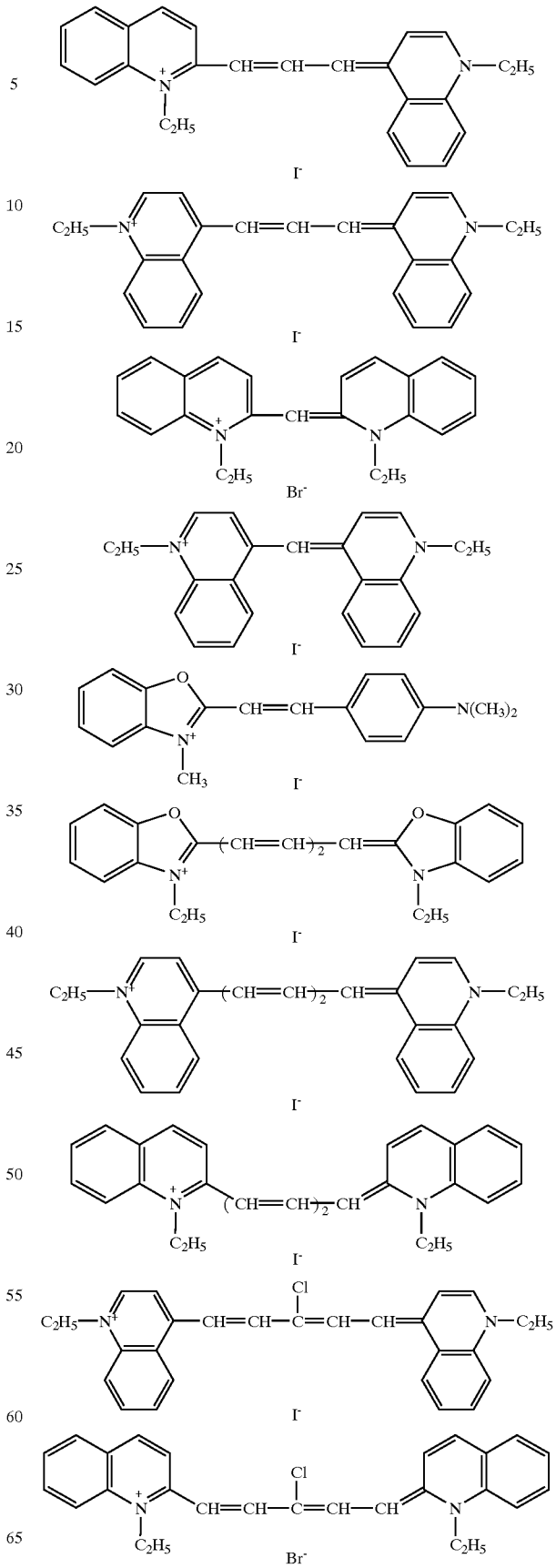

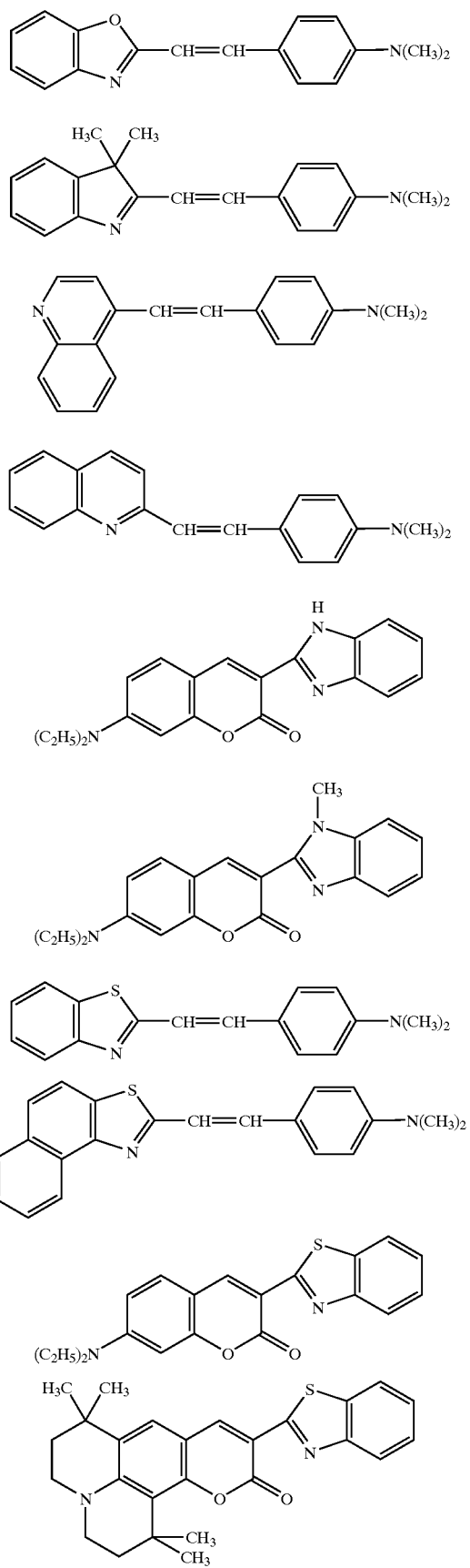
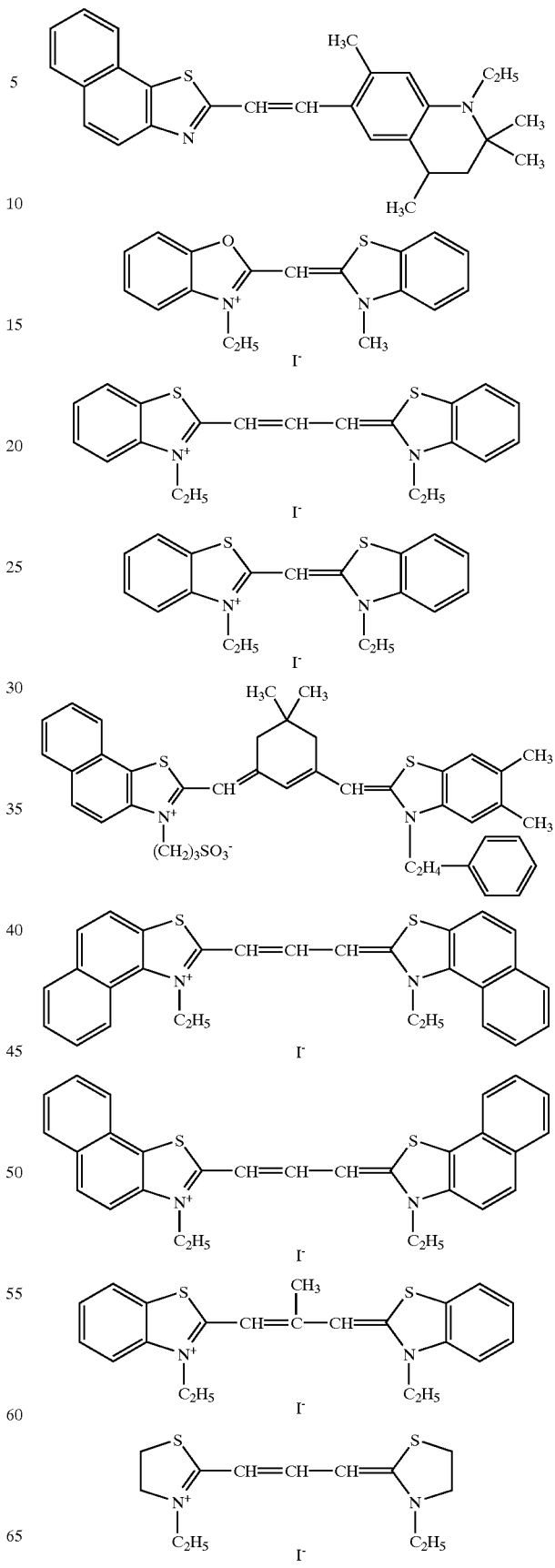

-continued

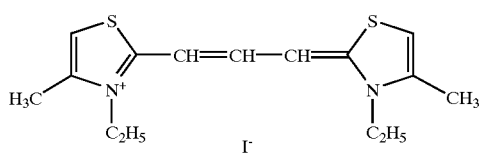
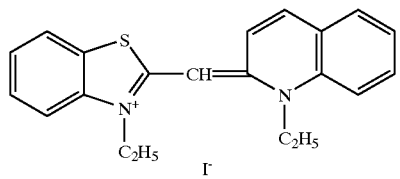
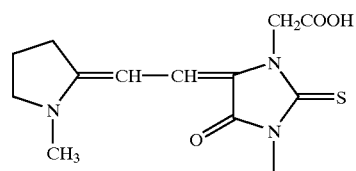
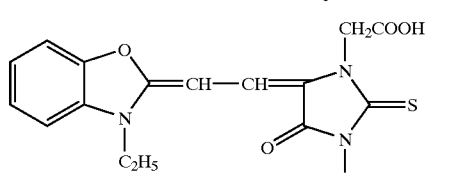
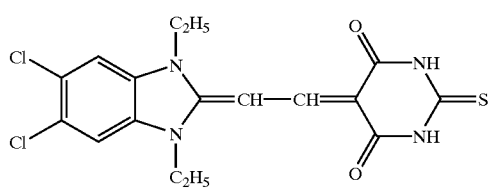
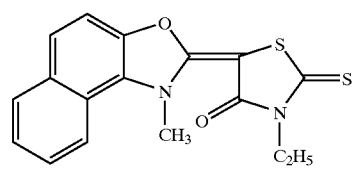
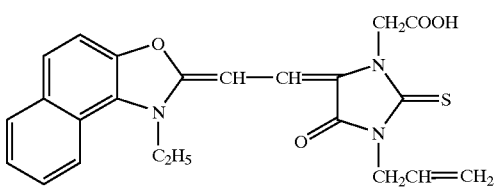
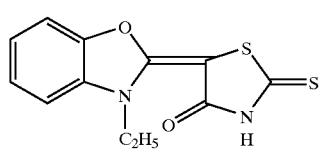
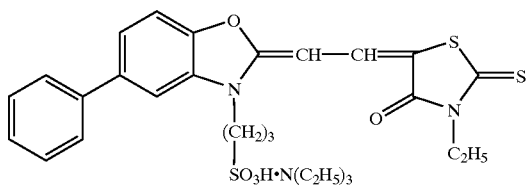

-continued

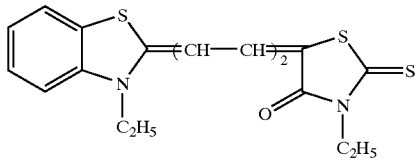
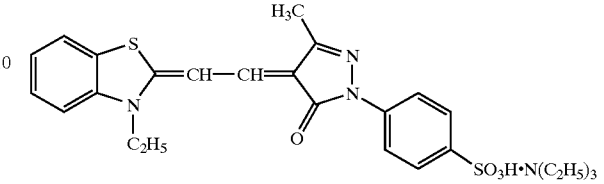
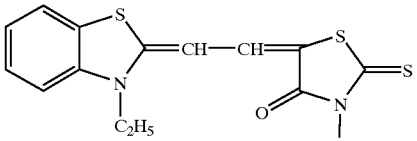
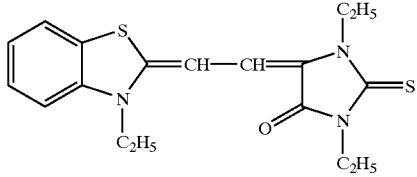
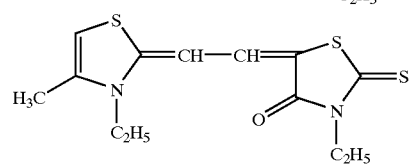
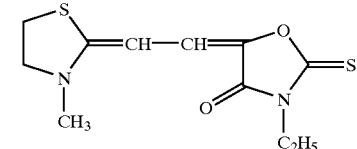
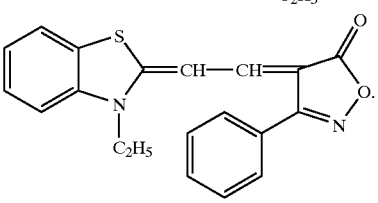

As a direct dye, at least one of these direct dyes (I) to (IV) can be used. It is also possible to use another direct dye in combination therewith. In particular, when the direct dye (I), (II), (III) or (IV) is a yellow dye, combination with red and blue dyes, when it is a red dye, combination with yellow and blue dyes, and when it is a blue dye, combination with yellow and red dyes, each makes it possible to dye the hair with a deep and highly lustrous dark brown or black color.

Examples of the direct dye other than the direct dyes (I) to (IV) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57 (C.I. 12719); and basic dyes as described in Japanese Patent Publication No. Sho 58-2204, Japanese Patent Application Laid-Open (Kokai) No. Hei 9-118832, Japanese Language Laid-Open Publication (PCT) No. Hei 8-501322 or Japanese Language Laid-Open Publication (PCT) No. Hei 8-507545.

The direct dyes (I) to (IV) are each preferably added in an amount of 0.01 to 20 wt. %, more preferably 0.05 to 10 wt. %, especially 0.1 to 5 wt. % based on the whole composition (after mixture of all the component parts when the hair dye composition is a two part or three part type; this will apply equally hereinafter). When another direct dye is added in combination, the content of it in total with the direct dye (I), (II), (III) or (IV) preferably ranges from 0.05 to 10 wt. %, especially 0.1 to 5 wt. %.

The hair dye composition of the present invention is preferably adjusted to pH 6 to 11, with pH 8 to 11 being especially preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, based on the whole composition.

In the hair dye composition of the present invention, an oxidation dye can be incorporated further. This incorporation enables markedly vivid dyeing not attainable by the single use of an oxidation dye. In this case, the above-exemplified oxidizing agents can be used as an oxidizing agent, with hydrogen peroxide being particularly preferred. Alternatively, an oxidizing enzyme such as laccase can be employed. For the oxidation dye, known color developers and couplers ordinarily employed for an oxidation type hair dye can be used.

Examples of the developer include p-phenylenediamines having one or several groups selected from groups $NH_2$—, NHR— and $NR_2$— (in which R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives; p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6=hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As each of a developer and a coupler, at least one of the above-exemplified ones can be used. Although no particular limitation is imposed on the content of each of them, it is added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention in the case where the direct dye (I) or (II) to be incorporated in the composition is a cationic dye, it is preferred to satisfy the following equation:

"Ion activity concentration of the anionic component/ion activity concentration of the cationic direct dye (I) or (II) incorporated in the hair dye composition≦8"

The term "ion activity concentration" as used herein means "molar concentration×ionic valence".

Addition of a polyol, polyol alkyl ether, cationic or amphoteric polymer or silicone to the hair dye composition of the present invention is preferred, because the resulting composition can dye the hair uniformly and improve the cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The direct dye (I), (II), (III) or (IV) can be incorporated in either one or both of these component parts of the two-part or three-part composition. When the hair dye composition of the present invention is one-part type, it is applied to the hair directly, while when it is a two- or three-part type, it is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mpa·s in the stage of application to the hair (after mixing of all the components when the hair dye composition is a two-part or three-part type).

EXAMPLES

Direct dyes (I) to (IV) [Compounds (a) to (g)] and another direct dyes [Compounds (i), (ii)] used in the below-described examples are as follows:

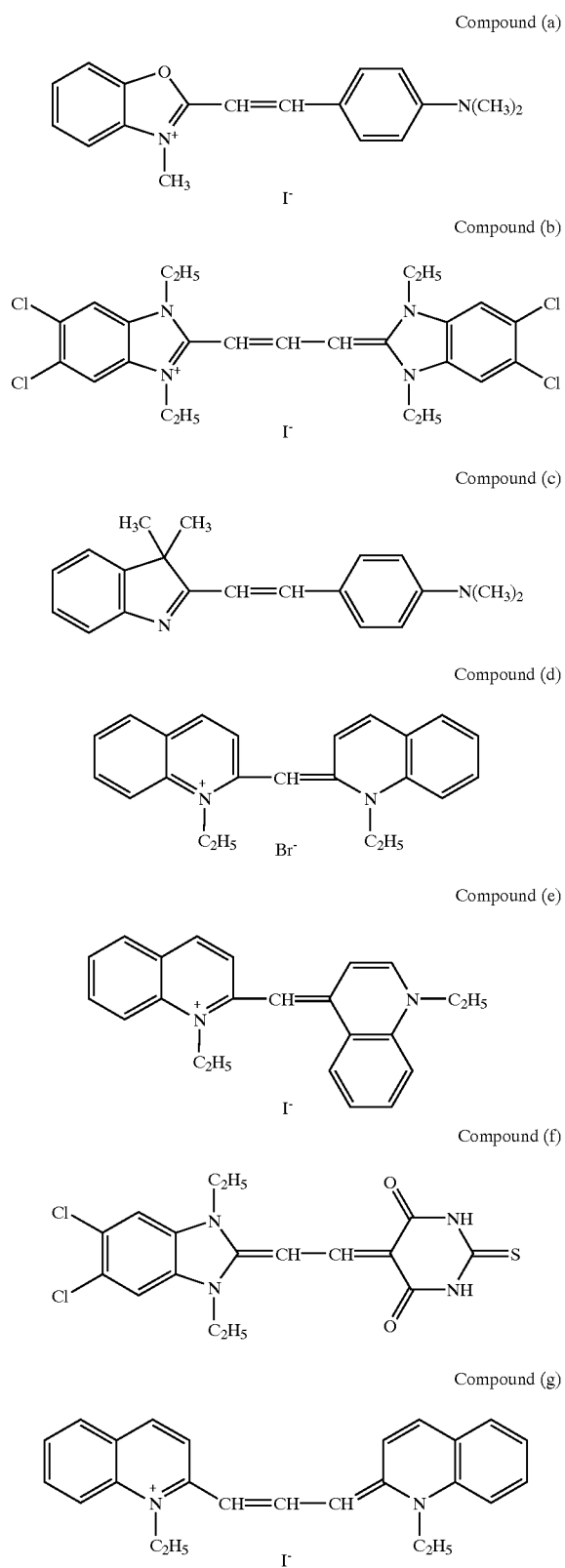

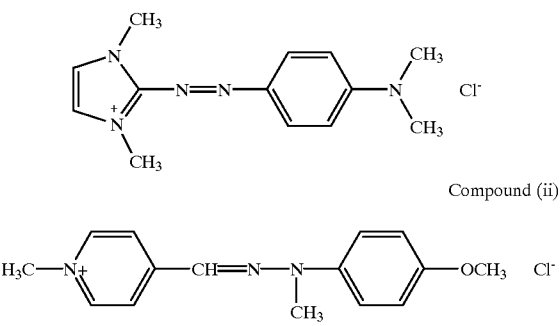

Examples 1 to 12

In a manner known per se in the art, hair dyes as shown in Tables 1 to 3 were prepared.

TABLE 1

| (wt. %) | Examples | | | | |
|---|---|---|---|---|---|
| | 1 | 2 | 3 | 4 | 5 |
| Dye [Compound (a)] | 0.2 | | 0.15 | 0.1 | |
| Dye [Compound (c)] | | 0.5 | | 0.1 | 0.2 |
| Dye [Compound (i), Red] | | | 0.15 | 0.1 | 0.05 |
| Dye [Compound (ii), Yellow] | | | 0.1 | 0.1 | |
| Ethanol | 5 | | | 5 | 5 |
| Propylene glycol | | | 5 | | 5 |
| Diethylene glycol monoethyl ether | | 10 | | | |
| Guar gum | 1 | | | | |
| Hydroxypropyl guar gum | | 1 | 1 | 1 | 1 |
| "Gufquat 734" (trade name; product of ISP Japan) | 1 | | 1 | | |
| "Catinal LC100" (trade name; product of Toho Chemical Industry) | | 1 | | | 1 |
| "Polyether-modified silicone KF6005" (trade name; product of Shin-Etsu Chemical) | | | | | 0.4 |
| "Amodimethicone SM8702C" (trade name; product of Dow Corning Toray Silicone) | | | | 1.5 | |
| Monoethanolamine | | | 0.1 | | |
| Phosphoric acid | Amount to adjust pH to 9 | | | | |
| Perfume | q.s. | | | | |
| Water | Balance | | | | |

TABLE 2

| | (wt. %) | Examples | | | |
|---|---|---|---|---|---|
| | | 6 | 7 | 8 | 9 |
| 1st part | Dye [Compound (b)] | 0.2 | | 0.15 | 0.2 |
| | Dye [Compound (d)] | | 0.1 | 0.15 | |
| | Dye [Compound (ii), Yellow] | | 0.1 | | 0.05 |
| | Dye [Basic Blue 99] | | | | 0.3 |
| | 28 wt. % Aqueous ammonia | | 5 | | |
| | Monoethanolamine | | 2 | | |
| | Propylene glycol | | 8 | | |
| | Polyoxyethylene (20) isostearyl ether | | 24 | | |
| | Polyoxyethylene (2) isostearyl ether | | 20 | | |
| | "Merquat 280" (trade name; product of Calgon Corp., a 35 wt. % aqueous solution) | 8 | | | |
| | "Polymer JR400" (trade name; product of Union Carbide) | | | 0.5 | 0.5 |
| | "Amodimethicone SM8702C" (trade name; product of Dow Corning Toray Silicone) | | | 2 | |

TABLE 2-continued

| (wt. %) | Examples | | | |
|---|---|---|---|---|
| | 6 | 7 | 8 | 9 |
| "Polyether modified silicone KF6005" (trade name; product of Shin-Etsu Chemical) | | | | 0.3 |
| Tetrasodium ethylenediaminetetraacetate | 0.1 | | | |
| Perfume | q.s. | | | |
| Ammonium chloride | Amount to adjust pH to 10 | | | |
| Water | Balance | | | |
| 2nd part 35 wt. % Aqueous hydrogen peroxide | 17.1 | | | |
| Methylparaben | 0.1 | | | |
| Phosphoric acid | Amount to adjust pH to 3.5 | | | |
| Water | Balance | | | |

TABLE 3

| (wt. %) | Examples | | |
|---|---|---|---|
| | 10 | 11 | 12 |
| 1st part Toluene-2,5-diamine | 1.9 | 1 | |
| Para-aminophenol | | | 1 |
| Resorcin | 2 | | |
| Para-amno-orhto-cresol | | | 1.1 |
| 2,4-Diaminophenoxyethanol | | 1.37 | |
| Dye [Compound (f)] | 0.05 | | |
| Dye [Compound (e)] | | 0.15 | |
| Dye [Compound (g)] | | | 0.1 |
| 28 wt. % Aqueous ammonia | | 5 | |
| Monoethanolamine | | 2 | |
| Propylene glycol | | 8 | |
| Polyoxyethylene (20) isostearyl ether | | 24 | |
| Polyoxyethylene (2) isostearyl ether | | 20 | |
| "Merquat 280" (trade name; product of Calgon Corp., a 35 wt. % aqueous solution) | 8 | | |
| "Polymer JR400" (trade name; product of Union Carbide) | | 0.5 | |
| "Amodimethicone SM8702C" (trade name; product of Dow Corning Toray Silicone) | | | 2 |
| Sodium sulfite | 0.05 | | |
| Ascorbic acid | 0.5 | | |
| Tetrasodium ethylenediaminetetraacetate | 0.1 | | |
| Perfume | q.s. | | |
| Ammonium chloride | Amount to adjust pH to 10 | | |
| Water | Balance | | |
| 2nd part 35 wt. % Aqueous hydrogen peroxide | 17.1 | | |
| Methylparaben | 0.1 | | |
| Phosphoric acid | Amount to adjust pH to 3.5 | | |
| Water | Balance | | |

Example 13

In a manner known per se in the art, the below-described hair dye was prepared.

| (First part) | (wt. %) |
|---|---|
| Para-aminophenol | 1 |
| Para-amino-ortho-cresol | 1.1 |
| Compound (d) | 0.1 |
| 28 wt. % Aqueous ammonia | 5 |
| Monoethanolamine | 2 |
| Cetanol | 8.5 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |
| Tetrasodium ethylenediaminetetraacetate | 0.1 |
| Perfume | q.s. |
| Ammonium chloride | Amount to adjust pH to 10 |
| Water | Balance |

| (Second part) | (wt. %) |
|---|---|
| 35 wt. % Aqueous hydrogen peroxide | 17.1 |
| Methylparaben | 0.1 |
| Phosphoric acid | Amount to adjust pH to 3.5 |
| Water | Balance |

What is claimed is:

1. A hair dye composition, comprising:

a one-part aqueous formulation containing a direct dye compound represented by formula (1), (II), (III) or (IV):

(I)

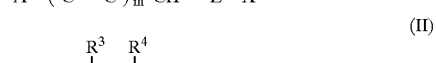

(II)

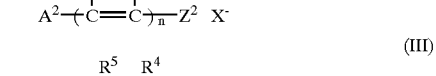

(III)

(IV)

wherein, m stands for 0, 1 or 2, n stands for 1 or 2, m units of $R^1$ and n units of $R^4$ each independently represents a hydrogen atom, a $C_{1-4}$ alkyl group or a halogen atom, m units of $R^2$ each independently represents a hydrogen atom, a $C_{1-4}$ alkyl group or an aryl group, with the proviso that at m=2, two $R^2$s, taken together with the adjacent =C—CH=C—, may form a carbocyclic structure or an oxygen-containing heterocyclic structure, n units of $R^3$ each independently represents a hydrogen atom or a $C_{1-4}$ alkyl group, n units of $R^5$ each independently represents a hydrogen atom or a $C_{1-4}$ alkyl group, or is bonded, via a group —CO—O—, to a ring $B^5$ to form a lactone ring, $R^6$ represents a hydrogen atom or a $C_{1-4}$ alkyl group, $A^1$ represents the below-described formula (1), (2) or (3), $A^2$ represents the below-described formula (4), $A^3$ represents the below-described formula (5), (6), (7), (8) or (9), $A^4$ and $Z^1$ each independently represents the below-described formula (10), (11), (12), (13), (14), (15) or (16), $Z^2$ represents the below-described formula (17), $Z^3$ represents the below-described formula (18), (19), (20) or (21):

A¹:
(1) 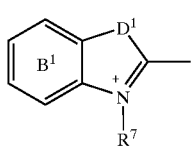
(2) 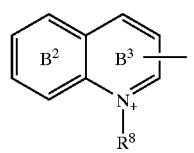
(3) 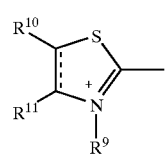
A²:
(4) 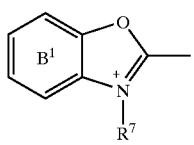
A³:
(5) 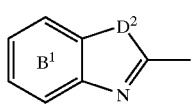
(6) 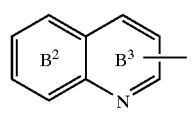
(7) 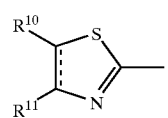
(8) 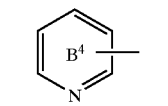
(9) 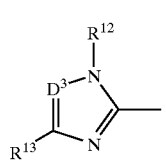
A⁴, Z¹:
(10) 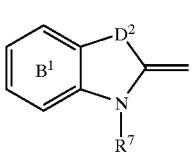
(11) 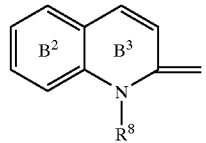
(12) 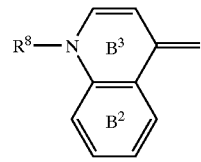
(13) 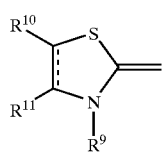
(14) 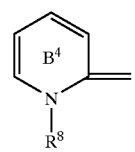
(15) 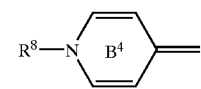
(16) 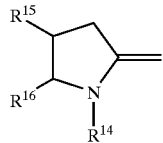
Z²:
(17) 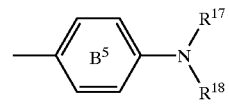
Z³:
(18) 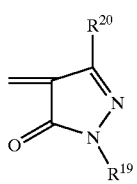
(19) 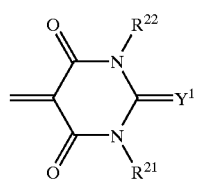

-continued

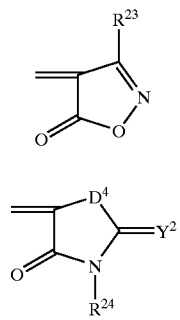

wherein a broken line means the presence or absence of bonding, $D^1$ represents an oxygen atom, a sulfur atom or a group $NR^{25}$, $D^2$ represents an oxygen atom, a sulfur atom, a group $NR^{26}$ or a group $CR^{27}R^{28}$, $D^3$ represents a nitrogen atom or a group $CR^{29}$, $D^4$ represents an oxygen atom, a sulfur atom or a group $NR^{30}$, $R^7$, $R^8$, $R^9$, $R^{14}$ and $R^{25}$ each independently represents a $C_{1-6}$ alkyl group which may have a substituent, $R^{10}$, $R^{11}$, $R^{13}$, $R^{15}$, $R^{16}$, $R^{21}$, $R^{22}$, $R^{27}$, $R^{28}$ and $R^{29}$ each independently represents a hydrogen atom or a $C_{1-6}$ alkyl group, $R^{12}$ and $R^{26}$ each independently represents a hydrogen atom or a $C_{1-6}$ alkyl group which may have a substituent, $R^{17}$ and $R^{18}$ each independently represents a hydrogen atom, a $C_{1-6}$ alkyl group which may have a substituent or an aryl group which may have a substituent, or $R^{17}$ and $R^{18}$, taken together with the adjacent nitrogen atom, form a nitrogen-containing heterocycle or one or both of $R^{17}$ and $R^{18}$ is (are) bonded to the ring $B^5$ to form a nitrogen-containing heterocycle, $R^{19}$ and $R^{23}$ each independently represents an aryl group which may have a substituent, $R^{20}$ represents a $C_{1-6}$ alkyl group, $R^{24}$ and $R^{30}$ each independently represents a hydrogen atom, a $C_{1-6}$ alkyl group which may have a substituent, or an aryl group which may have a substituent, $Y^1$ and $Y^2$ each independently represents an oxygen atom or a sulfur atom, rings $B^1$, $B^2$, $B^3$ and $B^4$ each independently has a ring structure which may have, as a substituent, a halogen atom, an aryl group or a $C_{1-4}$ alkyl group or may further be cyclocondensed with a benzene ring, $B^5$ has a ring structure which may have, as a substituent, a halogen atom, an aryl group or a $C_{1-4}$ alkyl group, may be condensed with a benzene ring, or may be bonded to $R^{17}$ or $R^{18}$ to have a ring structure which may be cyclocondensed with a nitrogen-containing heterocycle, and $X^-$ represents an anion, with the proviso that $X^-$ does not exist when $R^7$, $R^8$, $R^9$ and $R^{25}$ each has a sulfonium group as a substituent, the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers.

2. A hair dye composition, comprising:
a two-part aqueous formulation comprising, in a first part, a direct dye compound represented by formula (1), (II), (III) or (IV):

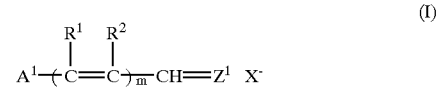

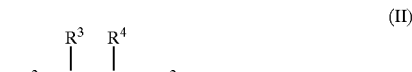

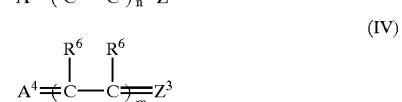

wherein, m stands for 0, 1 or 2, n stands for 1 or 2, m units of $R^1$ and n units of $R^4$ each independently represents a hydrogen atom, a $C_{1-4}$ alkyl group or a halogen atom, m units of $R^2$ each independently represents a hydrogen atom, a $C_{1-4}$ alkyl group or an aryl group, with the proviso that at m=2, two $R^2$s, taken together with the adjacent =C—CH=C—, may form a carbocyclic structure or an oxygen-containing heterocyclic structure, n units of $R^3$ each independently represents a hydrogen atom or a $C_{1-4}$ alkyl group, n units of $R^5$ each independently represents a hydrogen atom or a $C_{1-4}$ alkyl group, or is bonded, via a group —CO—O—, to a ring $B^5$ to form a lactone ring, $R^6$ represents a hydrogen atom or a $C_{1-4}$ alkyl group, $A^1$ represents the below-described formula (1), (2) or (3), $A^2$ represents the below-described formula (4), $A^3$ represents the below-described formula (5), (6), (7), (8) or (9), $A^4$ and $Z^1$ each independently represents the below-described formula (10), (11), (12), (13), (14), (15) or (16), $Z^2$ represents the below-described formula (17), $Z^3$ represents the below-described formula (18), (19), (20) or (21):

$A^1$:

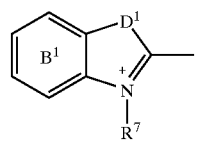

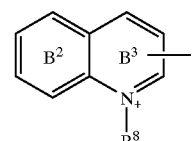

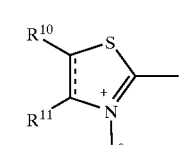

A²:

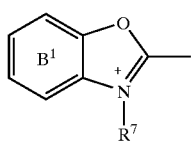 (4)

A³:

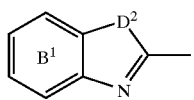 (5)

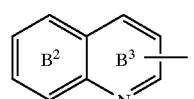 (6)

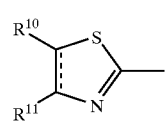 (7)

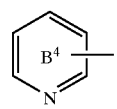 (8)

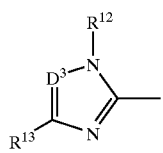 (9)

A⁴, Z¹:

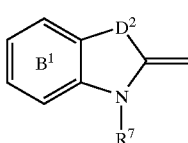 (10)

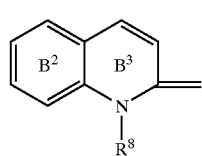 (11)

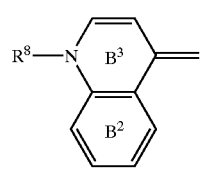 (12)

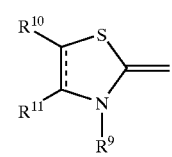 (13)

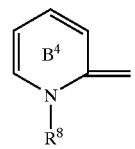 (14)

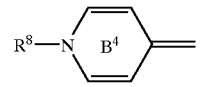 (15)

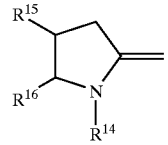 (16)

Z²:

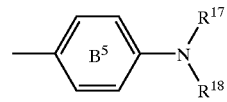 (17)

Z³:

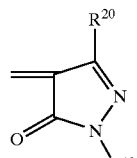 (18)

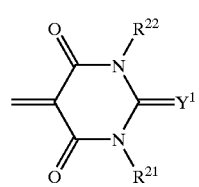 (19)

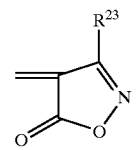 (20)

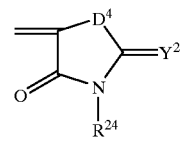 (21)

wherein a broken line means the presence or absence of bonding, $D^1$ represents an oxygen atom, a sulfur atom or a group $NR^{25}$, $D^2$ represents an oxygen atom, a sulfur atom, a group $NR^{26}$ or a group $CR^{27}R^{28}$, $D^3$ represents a nitrogen atom or a group $CR^{29}$, $D^4$ represents an oxygen atom, a sulfur atom or a group $NR^{30}$, $R^7$, $R^8$, $R^9$, $R^{14}$ and $R^{25}$ each independently represents a $C_{1-6}$ alkyl group which may have a substituent, $R^{10}$, $R^{11}$, $R^{13}$, $R^{15}$, $R^{16}$, $R^{21}$, $R^{22}$, $R^{27}$, $R^{28}$ and $R^{29}$ each independently represents a hydrogen atom or a $C_{1-6}$ alkyl group, $R^{12}$ and $R^{26}$ each independently represents a hydrogen atom or a $C_{1-6}$ alkyl group which may have a substituent, $R^{17}$ and $R^{18}$ each independently represents a hydrogen atom, a $C_{1-6}$ alkyl group which may have a substituent or an aryl group which may have a substituent, or $R^{17}$ and $R^{18}$, taken together with the adjacent nitrogen atom, form a nitrogen-containing heterocycle or one or both of $R^{17}$ and $R^{18}$ is (are) bonded to the ring $B^5$ to form a nitrogen-containing heterocycle, $R^{19}$ and $R^{23}$ each independently represents an aryl group which may have a substituent, $R^{20}$ represents a $C_{1-6}$ alkyl group, $R^{24}$ and $R^{30}$ each independently represents a hydrogen atom, a $C_{1-6}$ alkyl group which may have a substituent, or an aryl group which may have a substituent, $Y^1$ and $Y^2$ each independently represents an oxygen atom or a sulfur atom, rings $B^1$, $B^2$, $B^3$ and $B^4$ each independently has a ring structure which may have, as a substituent, a halogen atom, an aryl group or a $C_{1-4}$ alkyl group or may further be cyclocondensed with a benzene ring, $B^5$ has a ring structure which may have, as a substituent, a halogen atom, an aryl group or a $C_{1-4}$ alkyl group, may be condensed with a benzene ring, or may be bonded to $R^{17}$ or $R^{18}$ to have a ring structure which may be cyclocondensed with a nitrogen-containing heterocycle, and $X^-$ represents an anion, with the proviso that $X^-$ does not exist when $R^7$, $R^8$, $R^9$ and $R^{25}$ each has a sulfonium group as a substituent, the first part having a pH ranging from 6–11 that is adjusted to within said range by an alkali agent; and second part, comprising an aqueous solution of an oxidizing agent.

3. A hair dye composition, comprising:

a three-part aqueous formulation comprising, in a first part, a direct dye compound represented by formula (1), (II), (III) or (IV):

(I)

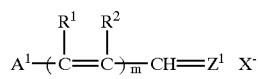

(II)

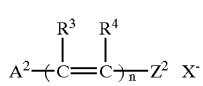

(III)

(IV)

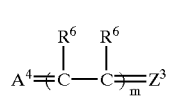

wherein, m stands for 0, 1 or 2, n stands for 1 or 2, m units of $R^1$ and n units of $R^4$ each independently represents a hydrogen atom, a $C_{1-4}$ alkyl group or a halogen atom, m units of $R^2$ each independently represents a hydrogen atom, a $C_{1-4}$ alkyl group or an aryl group, with the proviso that at m=2, two $R^2$s, taken together with the adjacent =C—CH=C—, may form a carbocyclic structure or an oxygen-containing heterocyclic structure, n units of $R^3$ each independently represents a hydrogen atom or a $C_{1-4}$ alkyl group, n units of $R^5$ each independently represents a hydrogen atom or a $C_{1-4}$ alkyl group, or is bonded, via a group —CO—O—, to a ring $B^5$ to form a lactone ring, $R^6$ represents a hydrogen atom or a $C_{1-4}$ alkyl group, $A^1$ represents the below-described formula (1), (2) or (3), $A^2$ represents the below-described formula (4), $A^3$ represents the below-described formula (5), (6), (7), (8) or (9), $A^4$ and $Z^1$ each independently represents the below-described formula (10), (11), (12), (13), (14), (15) or (16), $Z^2$ represents the below-described formula (17), $Z^3$ represents the below-described formula (18), (19), (20) or (21):

$A^1$:

(1)

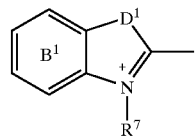

(2)

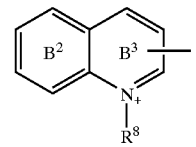

(3)

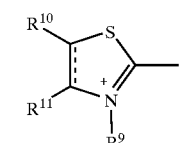

$A^2$:

(4)

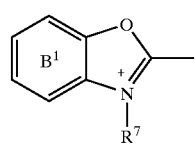

$A^3$:

(5)

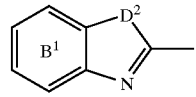

(6)

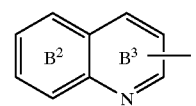

(7)

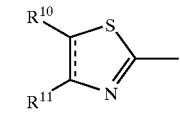

(8)

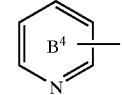

(9)

-continued

A⁴, Z¹:

(10) 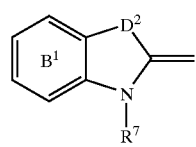

(11) 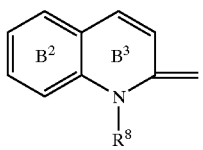

(12) 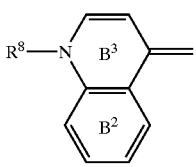

(13) 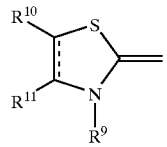

(14) 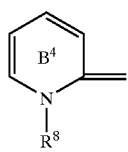

(15) 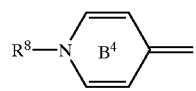

(16) 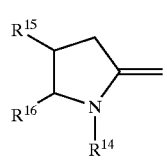

Z²:

(17) 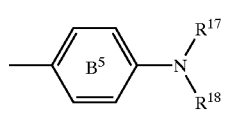

Z³:

(18) 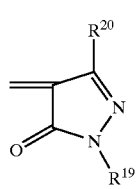

-continued

(19) 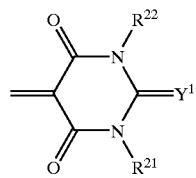

(20) 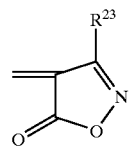

(21) 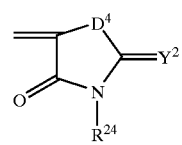

wherein a broken line means the presence or absence of bonding, $D^1$ represents an oxygen atom, a sulfur atom or a group $NR^{25}$, $D^2$ represents an oxygen atom, a sulfur atom, a group $NR^{26}$ or a group $CR^{27}R^{28}$, $D^3$ represents a nitrogen atom or a group $CR^{29}$, $D^4$ represents an oxygen atom, a sulfur atom or a group $NR^{30}$, $R^7$, $R^8$, $R^9$, $R^{14}$ and $R^{25}$ each independently represents a $C_{1-6}$ alkyl group which may have a substituent, $R^{10}$, $R^{11}$, $R^{13}$, $R^{15}$, $R^{16}$, $R^{21}$, $R^{22}$, $R^{27}$, $R^{28}$ and $R^{29}$ each independently represents a hydrogen atom or a $C_{1-6}$ alkyl group, $R^{12}$ and $R^{26}$ each independently represents a hydrogen atom or a $C_{1-6}$ alkyl group which may have a substituent, $R^{17}$ and $R^{18}$ each independently represents a hydrogen atom, a $C_{1-6}$ alkyl group which may have a substituent or an aryl group which may have a substituent, or $R^{17}$ and $R^{18}$, taken together with the adjacent nitrogen atom, form a nitrogen-containing heterocycle or one or both of $R^{17}$ and $R^{18}$ is (are) bonded to the ring $B^5$ to form a nitrogen-containing heterocycle, $R^{19}$ and $R^{23}$ each independently represents an aryl group which may have a substituent, $R^{20}$ represents a $C_{1-6}$ alkyl group, $R^{24}$ and $R^{30}$ each independently represents a hydrogen atom, a $C_{1-6}$ alkyl group which may have a substituent, or an aryl group which may have a substituent, $Y^1$ and $Y^2$ each independently represents an oxygen atom or a sulfur atom, rings $B^1$, $B^2$, $B^3$ and $B^4$ each independently has a ring structure which may have, as a substituent, a halogen atom, an aryl group or a $C_{1-4}$ alkyl group or may further be cyclocondensed with a benzene ring, $B^5$ has a ring structure which may have, as a substituent, a halogen atom, an aryl group or a $C_{1-4}$ alkyl group, may be condensed with a benzene ring, or may be bonded to $R^{17}$ or $R^{18}$ to have a ring structure which may be cyclocondensed with a nitrogen-containing heterocycle, and $X^-$ represents an anion, with the proviso that $X^-$ does not exist when $R^7$, $R^8$, $R^9$ and $R^{25}$ each has a sulfonium group as a substituent, the first part having a pH ranging from 6–11 that is adjusted to within said range by an alkali agent; and a second part, comprising an aqueous solution of an oxidizing agent; and a third part, comprising a powdered oxidizing agent.

4. The hair dye composition according to claim 1, wherein the content of alkali in the composition ranges from 0.01 to 20 wt % of the formulation.

5. The hair dye composition according to claim 2, wherein the oxidizing agent is hydrogen peroxide, a persulfate, a perborate, a percarbonate or a bromate.

6. The hair dye composition according to claim 2, wherein the oxidizing agent is present in the entire composition in an amount of 0.5 to 10 wt %.

7. The hair dye composition according to claim 2, wherein the oxidizing agent is combined with a developer and a coupler in the second part of the composition, each present in an amount ranging from 0.01 to 20 wt % of the entire composition.

8. The hair dye composition according to claim 3, wherein the oxidizing agent of the second part is hydrogen peroxide, a persulfate, a perborate, a percarbonate or a bromate.

9. The hair dye composition according to claim 3, wherein the oxidizing agent of the second part is present in the entire composition in an amount of 0.5 to 10 wt %.

10. The hair dye composition according to claim 3, wherein the oxidizing agent is combined with a developer and a coupler in the second part of the composition, each present in an amount ranging from 0.01 to 20 wt % of the entire composition.

11. The hair dye composition according to claim 3, wherein the third part of the composition contains a powdered persulfate oxidizing agent.

12. A method of dyeing hair, comprising:
treating the hair with a one-part aqueous formulation containing a direct dye compound represented by formula (1), (II), (III) or (IV):

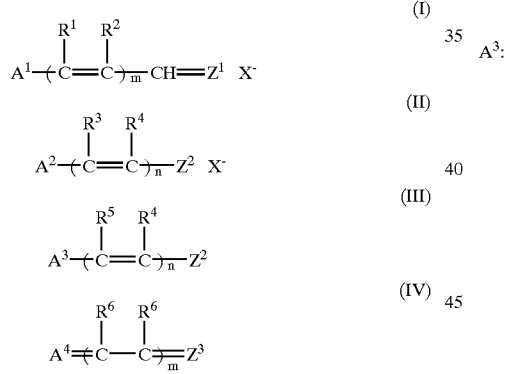

wherein, m stands for 0, 1 or 2, n stands for 1 or 2,
m units of $R^1$ and n units of $R^4$ each independently represents a hydrogen atom, a $C_{1-4}$ alkyl group or a halogen atom, m units of $R^2$ each independently represents a hydrogen atom, a $C_{1-4}$ alkyl group or an aryl group, with the proviso that at m=2, two $R^2$s, taken together with the adjacent =C—CH=C—, may form a carbocyclic structure or an oxygen-containing heterocyclic structure, n units of $R^3$ each independently represents a hydrogen atom or a $C_{1-4}$ alkyl group, n units of $R^5$ each independently represents a hydrogen atom or a $C_{1-4}$ alkyl group, or is bonded, via a group —CO—O—, to a ring $B^5$ to form a lactone ring, $R^6$ represents a hydrogen atom or a $C_{1-4}$ alkyl group,
$A^1$ represents the below-described formula (1), (2) or (3), $A^2$ represents the below-described formula (4), $A^3$ represents the below-described formula (5), (6), (7), (8) or (9), $A^4$ and $Z^1$ each independently represents the below-described formula (10), (11), (12), (13), (14), (15) or (16), $Z^2$ represents the below-described formula (17), $Z^3$ represents the below-described formula (18), (19), (20) or (21):

$A^1$:

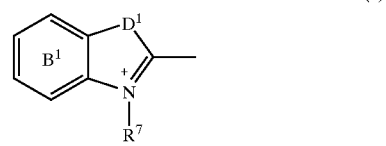
(1)

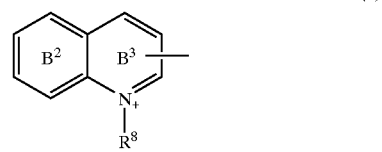
(2)

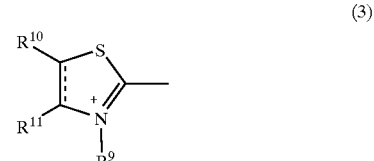
(3)

$A^2$:

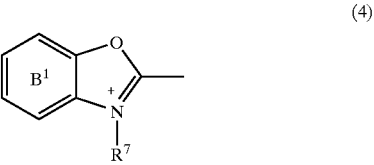
(4)

$A^3$:

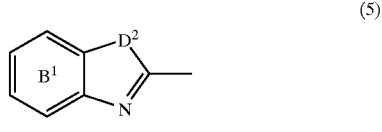
(5)

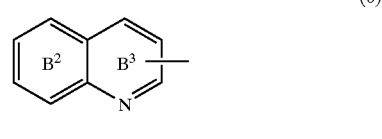
(6)

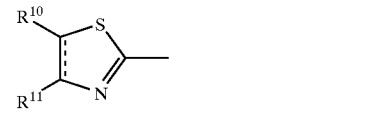
(7)

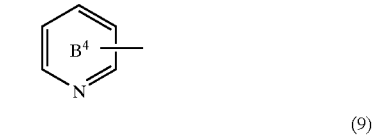
(8)

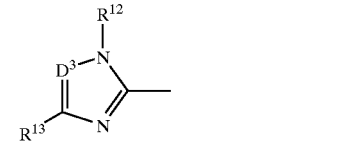
(9)

A⁴, Z¹:

(10) 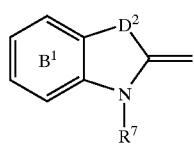

(11) 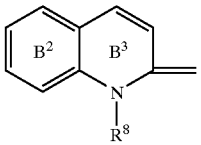

(12) 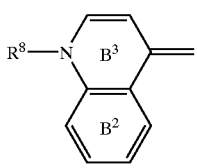

(13) 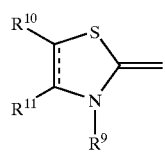

(14) 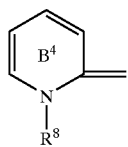

(15) 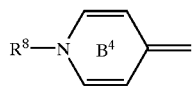

(16) 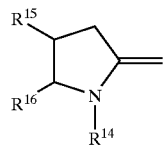

Z²:

(17) 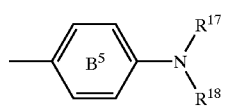

Z³:

(18) 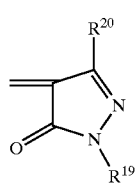

(19) 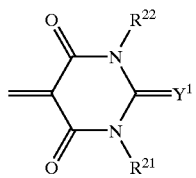

(20) 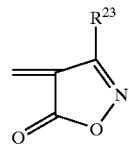

(21) 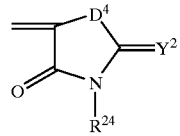

wherein a broken line means the presence or absence of bonding, $D^1$ represents an oxygen atom, a sulfur atom or a group $NR^{25}$, $D^2$ represents an oxygen atom, a sulfur atom, a group $NR^{26}$ or a group $CR^{27}R^{28}$, $D^3$ represents a nitrogen atom or a group $CR^{29}$, $D^4$ represents an oxygen atom, a sulfur atom or a group $NR^{30}$, $R^7$, $R^8$, $R^9$, $R^{14}$ and $R^{25}$ each independently represents a $C_{1-6}$ alkyl group which may have a substituent, $R^{10}$, $R^{11}$, $R^{13}$, $R^{15}$, $R^{16}$, $R^{21}$, $R^{22}$, $R^{27}$, $R^{28}$ and $R^{29}$ each independently represents a hydrogen atom or a $C_{1-6}$ alkyl group, $R^{12}$ and $R^{26}$ each independently represents a hydrogen atom or a $C_{1-6}$ alkyl group which may have a substituent, $R^{17}$ and $R^{18}$ each independently represents a hydrogen atom, a $C_{1-6}$ alkyl group which may have a substituent or an aryl group which may have a substituent, or $R^{17}$ and $R^{18}$, taken together with the adjacent nitrogen atom, form a nitrogen-containing heterocycle or one or both of $R^{17}$ and $R^{18}$ is (are) bonded to the ring $B^5$ to form a nitrogen-containing heterocycle, $R^{19}$ and $R^{23}$ each independently represents an aryl group which may have a substituent, $R^{20}$ represents a $C_{1-6}$ alkyl group, $R^{24}$ and $R^{30}$ each independently represents a hydrogen atom, a $C_{1-6}$ alkyl group which may have a substituent, or an aryl group which may have a substituent, $Y^1$ and $Y^2$ each independently represents an oxygen atom or a sulfur atom, rings $B^1$, $B^2$, $B^3$ and $B^4$ each independently has a ring structure which may have, as a substituent, a halogen atom, an aryl group or a $C_{1-4}$ alkyl group or may further be cyclocondensed with a benzene ring, $B^5$ has a ring structure which may have, as a substituent, a halogen atom, an aryl group or a $C_{1-4}$ alkyl group, may be condensed with a benzene ring, or may be bonded to $R^{17}$ or $R^{18}$ to have a ring structure which may be cyclocondensed with a nitrogen-containing heterocycle, and $X^-$ represents an anion, with the proviso that $X^-$ does not exist when $R^7$, $R^8$, $R^9$ and $R^{25}$ each has a sulfonium group as a substituent, the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers.

13. A method of dyeing hair, comprising:

treating the hair with a two-part aqueous formulation comprising, in a first part, a direct dye compound represented by formula (I), (II), (III) or (IV):

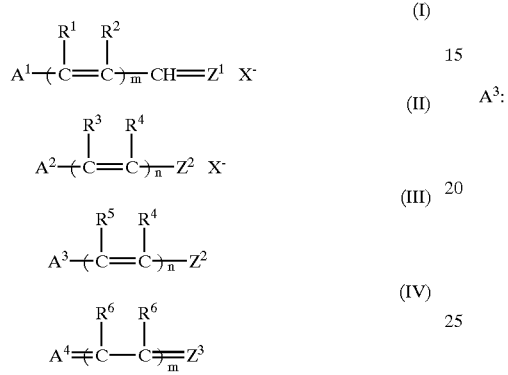

wherein, m stands for 0, 1 or 2, n stands for 1 or 2, m units of $R^1$ and n units of $R^4$ each independently represents a hydrogen atom, a $C_{1-4}$ alkyl group or a halogen atom, m units of $R^2$ each independently represents a hydrogen atom, a $C_{1-4}$ alkyl group or an aryl group, with the proviso that at m=2, two $R^2$s, taken together with the adjacent =C—CH=C—, may form a carbocyclic structure or an oxygen-containing heterocyclic structure, n units of $R^3$ each independently represents a hydrogen atom or a $C_{1-4}$ alkyl group, n units of $R^5$ each independently represents a hydrogen atom or a $C_{1-4}$ alkyl group, or is bonded, via a group —CO—O—, to a ring $B^5$ to form a lactone ring, $R^6$ represents a hydrogen atom or a $C_{1-4}$ alkyl group, $A^1$ represents the below-described formula (1), (2) or (3), $A^2$ represents the below-described formula (4), $A^3$ represents the below-described formula (5), (6), (7), (8) or (9), $A^4$ and $Z^1$ each independently represents the below-described formula (10), (11), (12), (13), (14), (15) or (16), $Z^2$ represents the below-described formula (17), $Z^3$ represents the below-described formula (18), (19), (20) or (21):

$A^1$:

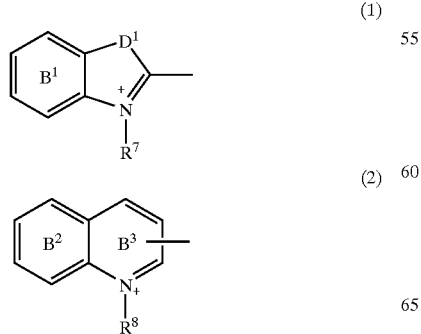

$A^2$:

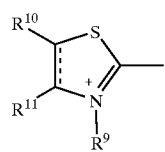

$A^3$:

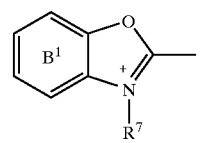

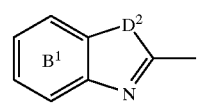

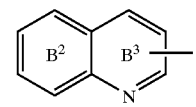

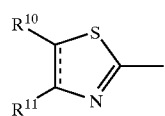

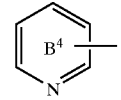

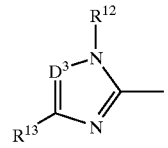

$A^4, Z^1$:

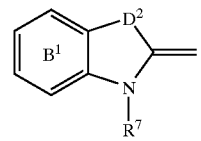

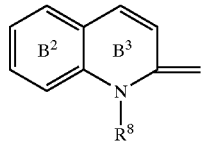

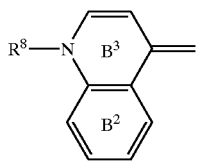

-continued

(13)
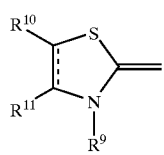

(14)
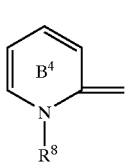

(15)
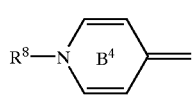

(16)
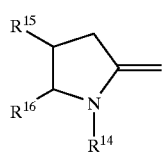

$Z^2$:

(17)
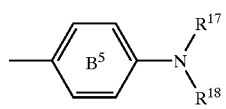

$Z^3$:

(18)
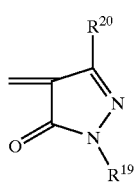

(19)
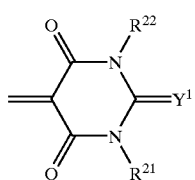

(20)
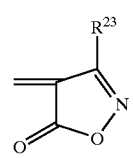

(21)
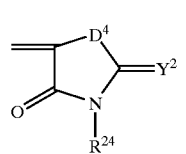

wherein a broken line means the presence or absence of bonding, $D^1$ represents an oxygen atom, a sulfur atom or a group $NR^{25}$, $D^2$ represents an oxygen atom, a sulfur atom, a group $NR^{26}$ or a group $CR^{27}R^{28}$, $D^3$ represents a nitrogen atom or a group $CR^{29}$, $D^4$ repre- sents an oxygen atom, a sulfur atom or a group $NR^{30}$, $R^7$, $R^8$, $R^9$, $R^{14}$ and $R^{25}$ each independently represents a $C_{1-6}$ alkyl group which may have a substituent, $R^{10}$, $R^{11}$, $R^{13}$, $R^{15}$, $R^{16}$, $R^{21}$, $R^{22}$, $R^{27}$, $R^{28}$ and $R^{29}$ each independently represents a hydrogen atom or a $C_{1-6}$ alkyl group, $R^{12}$ and $R^{26}$ each independently represents a hydrogen atom or a $C_{1-6}$ alkyl group which may have a substituent, $R^{17}$ and $R^{18}$ each independently represents a hydrogen atom, a $C_{1-6}$ alkyl group which may have a substituent or an aryl group which may have a substituent, or $R^{17}$ and $R^{18}$, taken together with the adjacent nitrogen atom, form a nitrogen-containing heterocycle or one or both of $R^{17}$ and $R^{18}$ is (are) bonded to the ring $B^5$ to form a nitrogen-containing heterocycle, $R^{19}$ and $R^{23}$ each independently represents an aryl group which may have a substituent, $R^{20}$ represents a $C_{1-6}$ alkyl group, $R^{24}$ and $R^{30}$ each independently represents a hydrogen atom, a $C_{1-6}$ alkyl group which may have a substituent, or an aryl group which may have a substituent, $Y^1$ and $Y^2$ each independently represents an oxygen atom or a sulfur atom, rings $B^1$, $B^2$, $B^3$ and $B^4$ each independently has a ring structure which may have, as a substituent, a halogen atom, an aryl group or a $C_{1-4}$ alkyl group or may further be cyclocondensed with a benzene ring, $B^5$ has a ring structure which may have, as a substituent, a halogen atom, an aryl group or a alkyl group, may be condensed with a benzene ring, or may be bonded to $R^{17}$ or $R^{18}$ to have a $C_{1-4}$ ring structure which may be cyclocondensed with a nitrogen-containing heterocycle, and $X^-$ represents an anion, with the proviso that $X^-$ does not exist when $R^7$, $R^8$, $R^9$ and $R^{25}$ each has a sulfonium group as a substituent, the first part having a pH ranging from 6–11 that is adjusted to within said range by an alkali agent; and a second part, comprising an aqueous solution of an oxidizing agent.

14. A method of dyeing hair, comprising:
treating the hair with a three-part aqueous formulation comprising, in a first part, a direct dye compound represented by formula (1), (II), (III) or (IV):

(I)
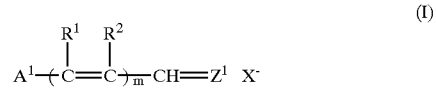

(II)
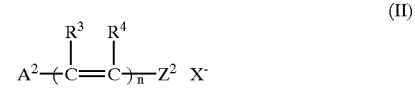

(III)

(IV)
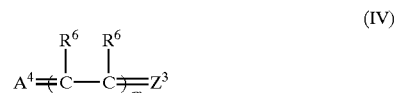

wherein, m stands for 0, 1 or 2, n stands for 1 or 2,
m units of $R^1$ and n units of $R^4$ each independently represents a hydrogen atom, a $C_{1-4}$ alkyl group or a halogen atom, m units of $R^2$ each independently represents a hydrogen atom, a $C_{1-4}$ alkyl group or an aryl group, with the proviso that at m=2, two $R^2$s, taken together with the adjacent =C—CH=C—, may form a carbocyclic structure or an oxygen-containing heterocyclic structure, n units of $R^3$ each independently represents a hydrogen atom or a $C_{1-4}$ alkyl group, n units of $R^5$ each independently represents a hydrogen atom or a $C_{1-4}$ alkyl group, or is bonded, via a group —CO—O—, to a ring $B^5$ to form a lactone ring, $R^6$ represents a hydrogen atom or a $C_{1-4}$ alkyl group, $A^1$ represents the below-described formula (1), (2) or (3), $A^2$ represents the below-described formula (4), $A^3$ represents the below-described formula (5), (6), (7), (8) or (9), $A^4$ and $Z^1$ each independently represents the below-described formula (10), (11), (12), (13), (14), (15) or (16), $Z^2$ represents the below-described formula (17), $Z^3$ represents the below-described formula (18), (19), (20) or (21):

$A^1$:

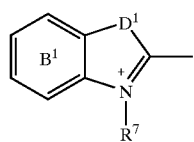
(1)

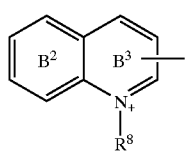
(2)

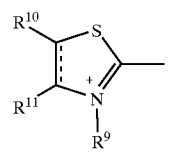
(3)

$A^2$:

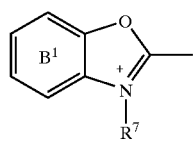
(4)

$A^3$:

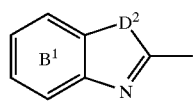
(5)

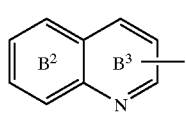
(6)

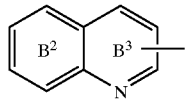
(7)

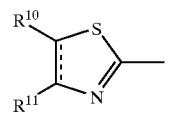
(8)

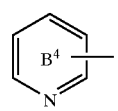

$A^4$, $Z^1$:

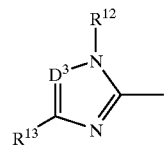
(9)

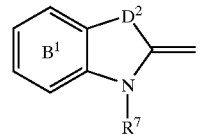
(10)

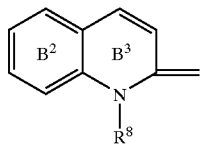
(11)

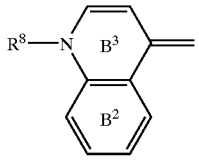
(12)

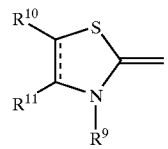
(13)

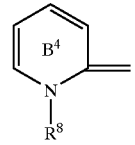
(14)

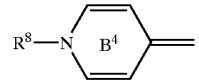
(15)

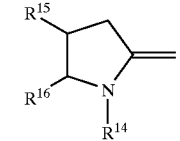
(16)

$Z^2$:

(17)

$Z^3$:

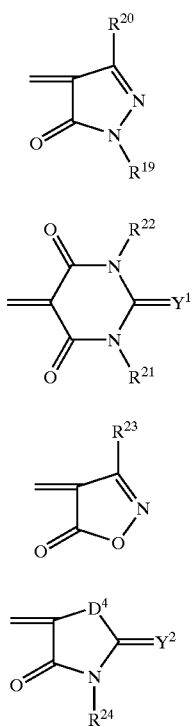

wherein a broken line means the presence or absence of bonding, $D^1$ represents an oxygen atom, a sulfur atom or a group $NR^{25}$, $D^2$ represents an oxygen atom, a sulfur atom, a group $NR^{26}$ or a group $CR^{27}R^{28}$, $D^3$ represents a nitrogen atom or a group $CR^{29}$, $D^4$ represents an oxygen atom, a sulfur atom or a group $NR^{30}$, $R^7$, $R^8$, $R^9$, $R^{14}$ and $R^{25}$ each independently represents a $C_{1-6}$ alkyl group which may have a substituent, $R^{10}$, $R^{11}$, $R^{13}$, $R^{15}$, $R^{16}$, $R^{21}$, $R^{22}$, $R^{27}$, $R^{28}$ and $R^{29}$ each independently represents a hydrogen atom or a $C_{1-6}$ alkyl group, $R^{12}$ and $R^{26}$ each independently represents a hydrogen atom or a $C_{1-6}$ alkyl group which may have a substituent, $R^{17}$ and $R^{18}$ each independently represents a hydrogen atom, a $C_{1-6}$ alkyl group which may have a substituent or an aryl group which may have a substituent, or $R^{17}$ and $R^{18}$, taken together with the adjacent nitrogen atom, form a nitrogen-containing heterocycle or one or both of $R^{17}$ and $R^{18}$ is (are) bonded to the ring $B^5$ to form a nitrogen-containing heterocycle, $R^{19}$ and $R^{23}$ each independently represents an aryl group which may have a substituent, $R^{20}$ represents a $C_{1-6}$ alkyl group, $R^{24}$ and $R^{30}$ each independently represents a hydrogen atom, a $C_{1-6}$ alkyl group which may have a substituent, or an aryl group which may have a substituent, $Y^1$ and $Y^2$ each independently represents an oxygen atom or a sulfur atom, rings $B^1$, $B^2$, $B^3$ and $B^4$ each independently has a ring structure which may have, as a substituent, a halogen atom, an aryl group or a $C_{1-4}$ alkyl group or may further be cyclocondensed with a benzene ring, $B^5$ has a ring structure which may have, as a substituent, a halogen atom, an aryl group or a $C_{1-4}$ alkyl group, may be condensed with a benzene ring, or may be bonded to $R^{17}$ or $R^{18}$ to have a ring structure which may be cyclocondensed with a nitrogen-containing heterocycle, and $X^-$ represents an anion, with the proviso that $X^-$ does not exist when $R^7$, $R^8$, $R^9$ and $R^{25}$ each has a sulfonium group as a substituent, the first part having a pH ranging from 6–11 that is adjusted to within said range by an alkali agent; and a second part, comprising an aqueous solution of an oxidizing agent; and a third part, comprising a powdered oxidizing agent.

* * * * *